United States Patent [19]

Speckman et al.

[11] Patent Number: 5,792,104
[45] Date of Patent: Aug. 11, 1998

[54] DUAL-RESERVOIR VASCULAR ACCESS PORT

[75] Inventors: Lori Cone Speckman, Ventura, Calif.; David A. Watson, East Greenwich, R.I.

[73] Assignee: Medtronic, Inc., Minneapolis, Minn.

[21] Appl. No.: 761,965

[22] Filed: Dec. 10, 1996

[51] Int. Cl.$^6$ .................................................. A61M 5/00
[52] U.S. Cl. ............................................. 604/93; 664/175
[58] Field of Search .................................. 604/93, 175, 82, 604/83, 167, 241–243

[56] References Cited

U.S. PATENT DOCUMENTS

| | | |
|---|---|---|
| 3,310,051 | 3/1967 | Schulte . |
| 3,724,882 | 4/1973 | Dehar . |
| 3,958,557 | 5/1976 | Sharp et al. . |
| 4,122,858 | 10/1978 | Schiff . |
| 4,133,312 | 1/1979 | Burd . |
| 4,190,040 | 2/1980 | Schulte . |
| 4,344,435 | 8/1982 | Aubin . |
| 4,405,305 | 9/1983 | Stephen et al. . |
| 4,405,320 | 9/1983 | Cracauer et al. . |
| 4,464,178 | 8/1984 | Dalton . |
| 4,564,222 | 1/1986 | Loker et al. . |
| 4,569,675 | 2/1986 | Prosl et al. . |
| 4,632,435 | 12/1986 | Polyak . |
| 4,673,394 | 6/1987 | Fenton, Jr. et al. . |
| 4,675,006 | 6/1987 | Hrushesky . |
| 4,681,560 | 7/1987 | Schulte et al. . |
| 4,685,905 | 8/1987 | Jeanneret . |
| 4,692,146 | 9/1987 | Hilger . |
| 4,693,707 | 9/1987 | Dye . |
| 4,695,273 | 9/1987 | Brown . |
| 4,695,276 | 9/1987 | Shimno et al. . |
| 4,704,103 | 11/1987 | Stober et al. . |
| 4,710,174 | 12/1987 | Moden et al. . |
| 4,723,948 | 2/1988 | Clark et al. . |
| 4,753,640 | 6/1988 | Nichols et al. . |
| 4,762,517 | 8/1988 | McIntyre et al. . |
| 4,772,270 | 9/1988 | Wiita et al. . |
| 4,772,276 | 9/1988 | Wiita et al. . |
| 4,778,447 | 10/1988 | Velde et al. . |
| 4,778,452 | 10/1988 | Moden et al. . |
| 4,781,693 | 11/1988 | Martinez et al. . |

(List continued on next page.)

FOREIGN PATENT DOCUMENTS 0 134 745  3/1985  European Pat. Off. .

OTHER PUBLICATIONS

M.R.I. Dual Implanted Port with Septum–Finder Ridge—Instructions for Use (2 pp.), Davol Inc., Issued Date: Feb. 1992.

Hickman Subcutaneous Port—Instructions for Use (3 pp.), Davol Inc., Revised Date: Feb., 1988.

The Port–A–Cath Implantable Drug Delivery System—Instructions for Use (4 pp.), Pharmacia Inc., Revised: Oct. 1986.

LifePort Vascular Access System—Instructions for Use, (7 pp.), Strato Medical Corporation, 1989.

IPI International Pain & Implants Vascular & Intraspinal Access Devices Product Catalog, 5 pp., Jun. 1995.

*Primary Examiner*—John D. Yasko
*Attorney, Agent, or Firm*—Kelly Bauersfeld Lowry & Kelley, LLP

[57] ABSTRACT

A subcutaneously implantable vascular access port includes a base which defines a plurality of fluid cavities separated by a dividing wall configured to provide an outlet duct for each fluid cavity, wherein the outlet ducts are staggered along the length of the dividing wall, a cap configured to receive the base and which includes a plurality of septum access apertures aligned with the fluid cavities, and a single self-sealing septum captured between the cap and the base. An outlet stem exits the base and communicates with the fluid cavities therein. The outlet stem has two prongs formed in a side-by-side configuration extending outwardly from the base. Fluid injected into a fluid cavity through the septum flows through a smooth transition region in which the cross-sectional area is smoothly reduced from the corresponding fluid cavity. A locking sleeve provides radial inward pressure upon the catheter which is slid over the outlet stem, thereby insuring that the catheter remains mounted on the outlet stem.

21 Claims, 2 Drawing Sheets

U.S. PATENT DOCUMENTS

| | | |
|---|---|---|
| 4,816,020 | 3/1989 | Brownell . |
| 4,820,288 | 4/1989 | Isono . |
| 4,822,341 | 4/1989 | Colone . |
| 4,826,477 | 5/1989 | Adams . |
| 4,861,341 | 8/1989 | Woodburn . |
| 4,880,414 | 11/1989 | Whipple . |
| 4,892,518 | 1/1990 | Cupp et al. . |
| 4,905,682 | 3/1990 | Khayat . |
| 4,911,696 | 3/1990 | Miyasaka et al. . |
| 4,915,690 | 4/1990 | Cone et al. . |
| 4,929,236 | 5/1990 | Sampson . |
| 4,955,861 | 9/1990 | Enegren et al. . |
| 4,963,133 | 10/1990 | Whipple . |
| 4,995,863 | 2/1991 | Nichols et al. . |
| 5,026,344 | 6/1991 | Dijkstra et al. . |
| 5,041,098 | 8/1991 | Loiterman et al. . |
| 5,045,060 | 9/1991 | Melsky et al. . |
| 5,084,015 | 1/1992 | Moriuchi . |
| 5,108,377 | 4/1992 | Cone et al. . |
| 5,129,891 | 7/1992 | Young . |
| 5,167,638 | 12/1992 | Felix et al. . |
| 5,178,612 | 1/1993 | Fenton, Jr. . |
| 5,213,574 | 5/1993 | Tucker . |
| 5,360,407 | 11/1994 | Leonard . |
| 5,387,192 | 2/1995 | Glantz et al. . |
| 5,399,168 | 3/1995 | Wadsworth, Jr. et al. . |
| 5,613,945 | 3/1997 | Cai et al. ................................ 604/93 |

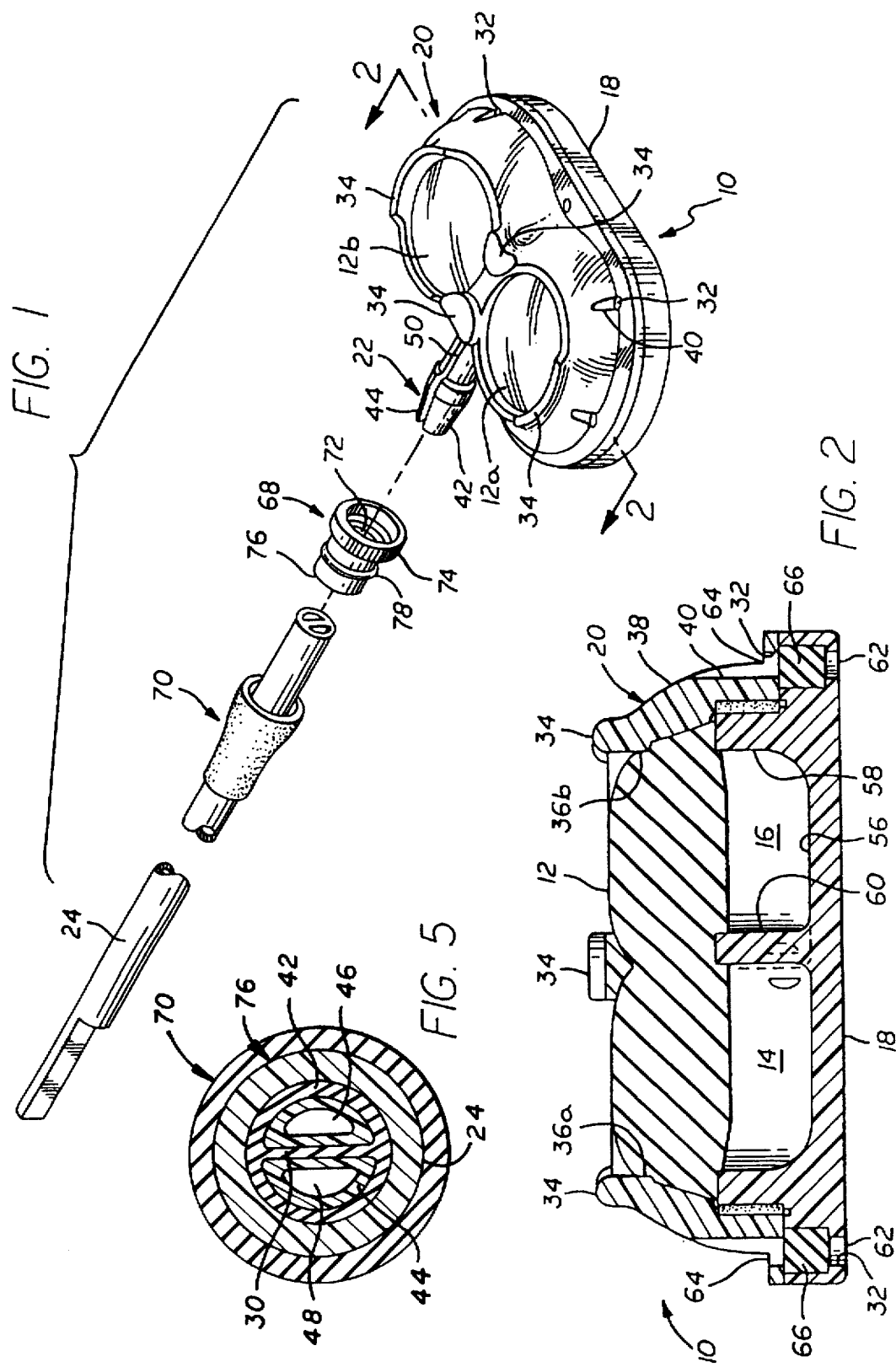

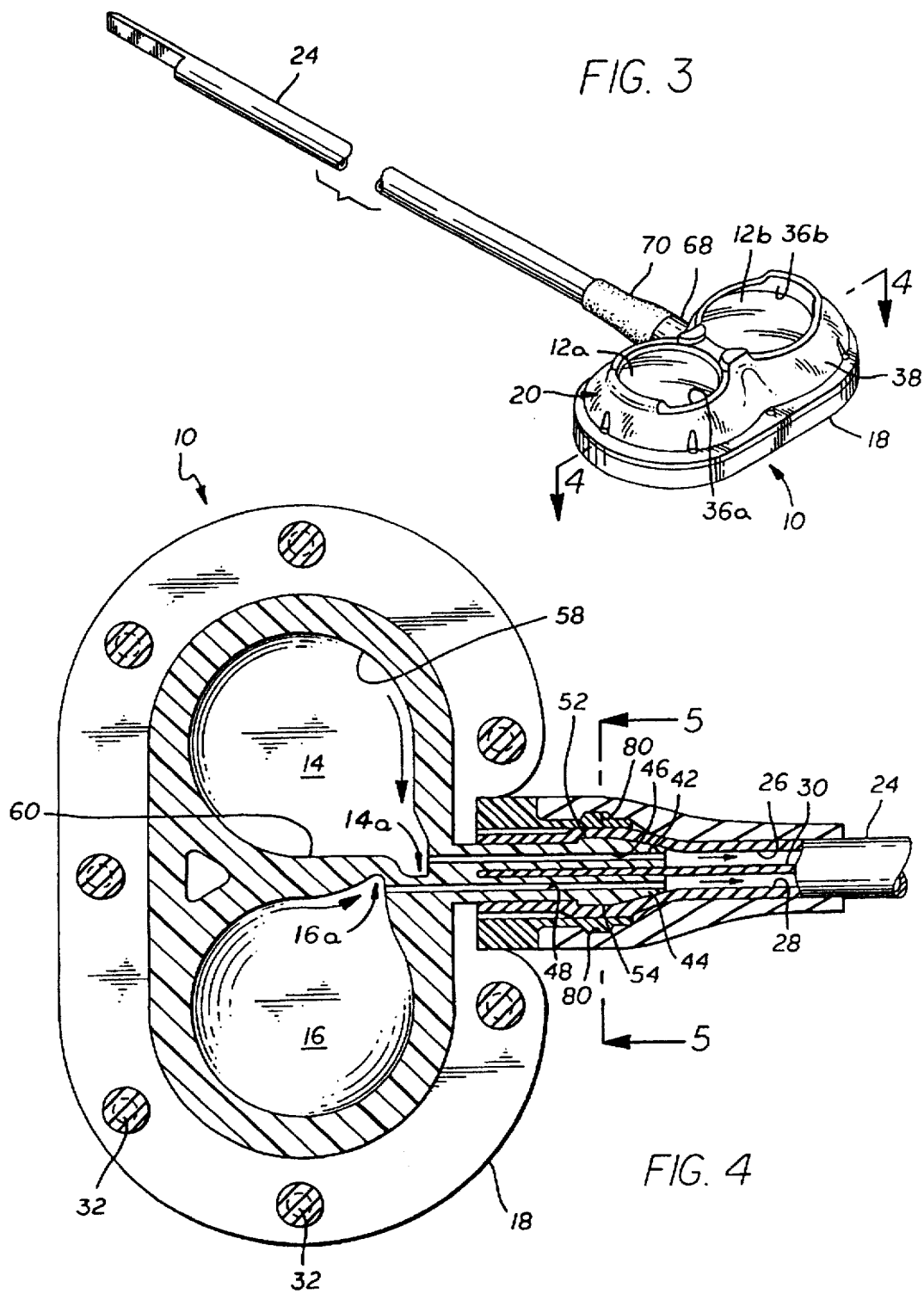

DUAL-RESERVOIR VASCULAR ACCESS PORT

BACKGROUND OF THE INVENTION

The present invention relates generally to a subcutaneously implantable vascular access port. More specifically, the present invention relates to an access port having a single needle-penetrable, self-sealing septum which affords repeated access to a plurality of distinct fluid cavities having staggered outlet ducts in communication with a plural lumen catheter.

A variety of implantable devices, known as subcutaneous access ports, are utilized to deliver fluids to or to withdraw fluids from the bloodstream of a patient. Such access ports typically include a needle-impenetrable housing which encloses one or more fluid cavities and defines for each such fluid cavity an access aperture communicating through the housing on the side thereof which is adjacent to the skin of the patient when the access port is implanted in the body. A needle-penetrable septum is received in and seals each access aperture. Exit passageways located in an outlet stem communicate with each of the fluid cavities for dispensing medication therefrom to a predetermined location in the body of the patient through an implanted catheter attached to the access port.

Once the access port and the catheter have been implanted beneath the skin of a patient, quantities of medication or blood may be dispensed from one such fluid cavity by means of a non-coring needle passed through the skin of the patient and penetrating the septum into one of the respective fluid cavities. This medication is directed through the distal end of the catheter to an entry point into the venous system of the body of the patient.

Blood may also be withdrawn for sampling from the body of a patient through such an access port. This is accomplished by piercing the skin of the patient and one of the respective septums with a non-coring needle and applying negative pressure thereto. This causes blood to be drawn through the catheter into the fluid cavity corresponding to the pierced septum and then out of the body of the patient through the needle.

To prevent clotting thereafter, the withdrawal route is flushed with a saline solution or heparin using again a non-coring needle piercing the skin of the patient and the septum in the same manner as if a medication were being infused.

Both intermittent and continual injections of medication may be dispensed by the access port. Continual access involves the use of a non-coring needle attached to an ambulatory-type pump or a gravity feed IV bag suspended above the patient. The ambulatory-type pump or the IV bag continually feeds the medication or fluid through the needle to the fluid cavity in the access port and from there through the catheter to the entry point into the venous system.

To facilitate locating each respective septum once the access port has been implanted, some access ports incorporate a raised circular ring located about the outer perimeter of the septum. This raised ring enhances the tactile sensation afforded by the subcutaneous septum to the palpating fingertip of a medical practitioner. Alternatively, other access ports have utilized palpation ridges rather than a raised circular ring for substantially the same purpose. The palpation ridges allow the location of the septum to be accurately determined when the access port is subcutaneously implanted.

To preclude reaction with the tissues in the body of patient, access ports are constructed of nonreactive materials, such as titanium or stainless steel. Although these materials are nonreactive, access ports constructed utilizing titanium or stainless steel materials produce an interfering or blurred image of the body of the patient in the vicinity of the implanted access port when diagnostic imaging techniques such as magnetic resonance imaging ("MRI"), CAT scans, or computerized tomography are used. The blurred region caused by the presence of a metallic access port in the body of a patient extends beyond the access port itself. Therefore, the use of metallic access ports limits the diagnostic imaging techniques that may be used relative to those areas of the body in which an access port is implanted. In place of metallic materials some access ports have been fabricated at least in part from biocompatible plastics.

A further problem relating to the materials for and manufacture of access ports is the deleterious impact of some manufacturing procedures on the fluids which flow through the fluid cavities and related structures located between the fluid cavities and the catheter. During the manufacture of an access port, whether the port is comprised of metallic or plastic materials, it becomes necessary to form the fluid cavities and exit passageways through which the fluid will be directed into the attached catheter. This manufacturing process often leaves sharp edges, seams and corners in the areas where the fluid cavity is to direct the flow of the fluid through an exit passageway. As blood or other fluids are injected through the septum into the fluid cavity, pressure developed within the fluid cavity tends to cause fluid to flow through the exit passageway. As the fluid in the fluid cavity flows past the sharp edges and corners produced in the manufacture of the access port, turbulence arises, taking the form of a vortex, adjacent to the sharp edges and corners. Some fluids, such as blood, are sensitive to this turbulence, and lysing of the red blood cell component of the injected blood can occur in these turbulent areas.

In addition, the production of the circular fluid cavities often results in the creation of areas within the housing in which fluid flow is retarded. These areas are referred to as dead spaces and usually occur in areas of transition, such as where the bottom of the septum interfaces with the walls of the fluid cavity and where the floor of the fluid cavity meets the exit passageway through which the fluid must flow. As the flow of fluids through dead spaces is retarded, stagnation occurs, resulting in some fluid being trapped within these dead spaces. If the access port is used to withdraw or transfuse blood, blood trapped in these dead spaces may form clots and block the flow of fluid through the fluid cavity.

Moreover, in some prior vascular access ports the internal reservoirs are formed by two plastic parts which are bonded together. This results in an undesirable seam being formed where the adjacent parts abut one another. The inside of the reservoir should be as smooth as possible to help prevent damage to blood cells or the initiation of blood clotting during infusion or withdrawal of blood through the port.

A further problem encountered in the design and construction of access port relates to the positioning of the septums within the housing of the access port. The positioning of the septums within the housing is a compromise between two conflicting objectives. These are the need to separate the septums to such a distance so that the septums may be easily differentiated for the purpose of injection and the need to restrict the overall dimensions of the access port for patient comfort and aesthetics. The distancing of the septums to facilitate their differentiation, however, results in a corresponding distancing of the fluid cavities. This result is at odds with another structural requirement for access ports with plural cavities, namely that the exit passageways from each fluid cavity be closely spaced at the point where the implanted catheter is to be coupled to the access port.

To guide the flow of a fluid from each of the spatially separated fluid cavities into the side-by-side configuration of fluid outflow necessitated by the dimensions of a plural lumen catheter, intermediate structural members have been required. Naturally, this complicates the process of manufacture and increases its cost, as well as the chances of structural failure.

There are several examples of such intermediate members used to resolve the manufacturing constraints imposed upon the construction of a passageway flowing from spatially separate fluid cavities into a side-by-side configuration acceptable by a catheter. One is to produce passageways in the form of bent metal tubes which are then insert molded or welded into the larger body of the access port. The use of such a metal component will interfere with the production of an access port which is free of limits as to the diagnostic imaging techniques that may be used relative to those areas of the body in which an access port is implanted. In addition, the non-integral nature of such metal outlet passageways raises the possibility of leakage of medication through the interstices between the metal tubes and the body of the access port.

Alternatively, to produce fluid flow from spatially separated fluid cavities into the closely spaced lumens of a catheter, each fluid cavity has been designed with its own spatially separated outlet stem. These outlet stems are then coupled by a hub structure for permanent attachment to the closely spaced lumens of a catheter. This type of arrangement increases the size of the overall access port and its cost of manufacture by adding thereto the necessity of fabricating and assembling of the hub element. Port connections to catheters in this manner are permanent. Accordingly, if the catheter is to be shortened by trimming, that trimming must occur at the distal end of the catheter, and this precludes the use thereat of any type of specially designed tip or valve.

An additional set of problems encountered in the use of access ports relates to the actual connection of the catheter to the access port. This is most commonly effected by securing the catheter to an outlet stem protruding from the housing of the access port. In an attempt to lock the catheter to the outlet stem of the access port, thread-type systems have been developed wherein the catheter is attached to an outlet stem, and the outlet stem is then threaded into the access port. When utilizing this system, however, it is difficult to determine the amount of engagement of the catheter onto the outlet stem. Some catheter connection systems do not allow visual verification of attachment. As a result, leakage and failure can occur.

To overcome this problem, access ports are produced in which the catheter is pre-attached at the factory. While this practice alleviates many of the problems with leakage and failure due to catheter slippage, this system severely limits the type of the catheter usable with the access port. This precludes the use of catheters having specialized distal tips, as the distal end of the catheter is the only end that can then be trimmed to effect its ultimate sizing. For example, catheters utilizing a Groshong® slit valve at their distal end may not have any of the distal tip of the catheter removed without compromising the catheter.

Accordingly, there has been a need for an improved vascular access port which overcomes the above-noted problems, and which can be manufactured economically. The present invention fulfills these needs and provides other related advantages.

SUMMARY OF THE INVENTION

The present invention resides in an improved dual reservoir vascular access port manufactured totally of plastic components, which provides secure attachment of a dual-lumen catheter to an outlet stem, and which further utilizes a single septum captured between a cap and a base to provide a fluid seal between a plurality of fluid cavities and a plurality of septum access apertures. The construction of the dual reservoir vascular port advantageously eliminates the need of a separate septum support to be joined to a base, thereby eliminating an undesirable seam within the fluid cavities. The implantable access port is capable of being implanted beneath the skin of a patient and enabling repeated, non-destructive fluid communication between the tip of a hypodermic needle piercing the skin of the patient and a proximal end of a selected one of the lumens of the dual lumen catheter implanted in the body of the patient and coupled to the access port. The dual lumen vascular access port of the present invention permits a medical practitioner to selectively inject a fluid from the needle into the body of the patient by producing a flow of the fluid from the tip of the needle, through the access port, and along the selected one of the lumens to the distal end of the catheter. Alternatively, the vascular access port permits a medical practitioner to selectively withdraw fluid from the body of the patient by producing a flow of the fluid from a distal end of a selected one of the lumens, through the access port and through the tip of the needle inserted into a selected fluid cavity.

Broadly, the vascular access port of the present invention comprises a base defining a plurality of fluid cavities having staggered outlet ducts, a cap configured to receive the base therein, a septum captured between the cap and the base, and an outlet from each fluid cavity outlet duct through the base. The cap includes a plurality of septum access apertures aligned with the plurality of fluid cavities. The septum provides a fluid seal between the plurality of fluid cavities and the plurality of septum access apertures.

In a preferred form of the invention, the base is formed of a needle-impenetrable material, and has a flat interior floor and walls normal to and upstanding therefrom. The walls define a first fluid cavity and a second fluid cavity separated by a dividing wall configured to provide a first outlet duct for the first fluid cavity and a second outlet duct for the second fluid cavity, wherein the first and second outlet ducts are staggered along the length of the dividing wall. Further, the upper surfaces of the walls support the septum thereon and are coplanar.

The cap is likewise formed of a needle-impenetrable material and includes a first circular septum access aperture aligned with the first fluid cavity, and a second circular septum access aperture aligned with the second fluid cavity. A plurality of palpation ridges extend upwardly from the cap to enable a medical practitioner to quickly determine the location of the septum access apertures when the vascular access port is subcutaneously implanted.

The cap and the base are preferably ultrasonically welded to one another, and include aligned apertures which define suture holes about the periphery of the vascular access port. The suture holes are filled with a silicone elastomer material.

The outlet comprises an outlet stem connected at a proximal end thereof with the base and configured at a distal end thereof to receive a proximal end of a dual lumen catheter. The stem encloses a pair of channels of different lengths which extend in side-by-side relationship betwdistal endistal end of the stem and a respective fluid cavity outlet duct. The channels are separated laterally a distance substantially equal to the lateral separation of the lumens in the catheter.

Means are further provided for locking the proximal end of the catheter to the outlet stem. The locking means includes a rigid catheter lock which is slidable over the proximal end of the catheter for positioning the catheter lock adjacent to the base. The locking means further includes a resiliently flexible strain relief sleeve which is positionable over adjoining portions of the catheter lock and the catheter. The catheter lock includes a distal tube section having a securement ridge, which is fitted within an internal groove of the strain relief sleeve.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a partially fragmented and partially exploded perspective view of a dual reservoir vascular access port embodying the invention;

FIG. 2 is an enlarged vertical section taken generally along the line 2—2 of FIG. 1;

FIG. 3 is a perspective view of the vascular access port of FIG. 1, illustrating attachment of a dual lumen catheter to an outlet stem;

FIG. 4 is an enlarged, fragmented partially sectional view taken generally along the line 4—4 of FIG. 3; and FIG. 5 is an enlarged sectional view taken generally along the line 5—5 of FIG. 4.

DETAILED DESCRIPTION OF THE PREFERRED EMBODIMENT

As shown in the drawings for purposes of illustration, the present invention is concerned with a dual-reservoir vascular access port, generally designated in the accompanying drawings by the reference number 10. The vascular access port 10 is similar in its construction and operation to the implantable plural fluid cavity port shown and described in U.S. Pat. No. 5,399,168, the contents of which are incorporated herein. In contrast with the prior art, the vascular access port 10 of the present invention advantageously utilizes a single silicone elastomer septum 12 to provide access to a plurality of fluid cavities 14 and 16 having staggered outlet ducts 14a and 16a, provided in a base 18. The septum 12 is captured between the base 18 and a rigid septum cap 20 which is bonded to the base by an ultrasonic weld or the like to form a fluid-tight seal.

The base 18 includes an outlet stem 22 by which a catheter 24 is coupled to the access port 10 and placed in fluid communication with the fluid cavities 14 and 16. The catheter 24 is dual lumen catheter with the lumens 26 and 28 thereof separated by a web 30.

In use, the distal end of the catheter 24 is entered into a major vessel of the cardiovascular system of a patient and advanced therefrom, for example, into a position at the superior vena cava. After the catheter 24 is thusly positioned, sufficient slack to allow for normal body movement without straining the catheter 24 is left in the point of entry of the catheter into the vascular system. The free end of the catheter 24 is then tunneled from its point of entry into the vascular system to a pocket in the tissue of a patient. The catheter 24 is then attached to the access port 10, and the access port is secured into the pocket using sutures installed through suture holes 32 provided through the base 18.

Generally, the access port 10 is placed in the chest wall (infraclavicular) on either the right or the left side supported by the underling ribs. A pocket incision is made about the diameter of the base 18. Preferably, the access port 10 is buried only about 0.50 inch below the skin, which is generally sufficient to prevent the access port from eroding through the skin. The incision is then closed.

The septum 12 serves to provide a fluid seal over each of the fluid cavities 14 and 16, and the septum cap 20 effectively delineates the portions of the septum 12 that may be punctured in order to gain access to the respective fluid cavities 14 and 16. In this regard, the septum 12 is configured such that it may be punctured by a non-coring needle, and re-sealed after the needle has been removed. The septum 12 is therefore constructed from a self-sealing polymer such as a silicone rubber.

The tactile locating of the septum sections 12a and 12b overlying the respective fluid cavities 14 and 16 is facilitated through the use of raised palpation ridges 34 which extend upwardly from the septum cap 20. The palpation ridges 34 are positioned closely adjacent to apertures 36 through the septum cap 20 which apertures provide access to the septum 12.

The vascular access port 10 is preferably constructed of a plastic material which does not interfere with MRI or CAT scan diagnostic imaging. The septum cap 20, preferably manufactured of a polyoxymethylene resin, is comprised of a top wall having formed therein a first septum access aperture 36a at a position opposite the first fluid cavity 14 in the base 18, and a second septum access aperture 36b positioned opposite the second fluid cavity 16. A skirt 38 depends from the top wall of the septum cap 20 to enclose the septum 12 and an upper portion of the base 18. The skirt 38 includes recesses 40 in alignment with the suture holes 32 through the base 18, to provide unrestricted access to the sutures holes 32.

The outlet stem 22 of the base 18 includes a pair of prongs 42 and 44 through which channels 46 and 48 of different lengths are provided to couple the catheter 24 to the access port 10. Generally the shape of the interior of the lumens 26 and 28 correspond to the exterior surfaces of the prongs 42 and 44. Likewise, a slot 50 between the prongs 42 and 44 corresponds in size and shape to the web 30 between the lumens 26 and 28 of the catheter 24. The entry of the web 30 into the slot 50 results in pressure from the radial exterior wall of the catheter 24 forcing the exterior surfaces of the prongs 42 and 44 inwardly into the web 30.

The base 18 has a flat floor 56 and generally curved walls 58 normal to and upstanding therefrom. The walls 58 define the fluid cavities 14 and 16 having non-circular cross sections when taken at a plane parallel to the floor 56 (see FIG. 4). The upper surfaces of the base 18 are co-planar and provide a support shelf for the septum 12. A dividing wall 60 separates the first fluid cavity 14 from the second fluid cavity 16. The dividing wall 60 is configured to provide the first outlet duct 14a for the first fluid cavity 14 and the second outlet duct 16a for the second fluid cavity 16, wherein the first and second outlet ducts are staggered along the length of the dividing wall.

The importance of having the first and second outlet ducts 14a and 16a staggered along the length of the dividing wall 60 is best understood in the context of molding of the base 18. During molding of the base 18, small metal pins fill the spaces which become the channels 46 and 48. In the molding process, the pins are inserted into the mold, the plastic is injected, the pins are withdrawn, and the base 18 is ejected from the mold. For the small-size catheters 24 required for the vascular system, relatively long, thin pins are utilized which slide in and out of the mold approximately every thirty seconds. Due to the size of the pins, they are fairly flexible. The pins must meet up with pieces of metal or "buttons" that form the fluid cavities 14 and 16 of the base 18. Due to pin flexibility and bending, the target for the end of the pins must be larger than pins themselves. Therefore the "buttons" must extend past the edge of the pins for the mold to function properly over time.

The gap between the buttons in the mold (which gap forms the dividing wall 60) should be as large as possible to facilitate the flow of plastic into the mold to form the base 18. A larger gap between the buttons also results in a thicker dividing wall 60. However, in prior art designs, the goals of (1) increasing the gap between the buttons, and (2) extending the buttons past the edge of the pins have been mutually exclusive. The present invention, however, successfully addresses these two goals. By staggering the areas on the buttons where the pins are inserted, each button can extend farther toward the center-line of the part, without overly decreasing the gap between the two buttons. This is made possible by configuring the dividing wall 60 to stagger the first and second outlet ducts 14a and 16a along the length of the dividing wall.

The suture holes 32 are defined by aligned apertures 62 and 64 provided in the base 18 and septum cap 20. Intermediate these aligned apertures 62 and 64 is an area filled with a silicone material 66. This particular construction of the suture hole 32 prevents tissue growth therethrough which facilitates surgical removal of the access port 10 when it is no longer needed.

To ensure a fluid tight seal between the catheter 24 and the outlet stem 22, a catheter lock 68 constructed from a rigid plastic such as polyoxy-methylene and a silicone elastomer strain relief sleeve 70 are utilized. The catheter lock 68 includes an internal passageway 72 through which the catheter 24 extends, a proximal base section 74 and a distal tubular section 76 which extends from the base section and includes a securement ridge 78. The strain relief sleeve 70 minimizes kinking of the catheter 24 at the end of the outlet stem 22.

Once the dual lumen catheter 24 has been fully placed over the length of the outlet stem 22 such that the prongs 42 and 44 are fully inserted into respective lumens 26 and 28, the catheter lock 68 is slid over the assembled catheter and outlet stem 22 to place the proximal base section 74 adjacent to the base 18 of the vascular access port 10. The internal configuration of the catheter lock 68 causes a compression of the catheter 24 relative to the outlet stem 22 at the barbs 52 and 54, forming a friction lock between the catheter lock 68, the catheter 24 and the outlet stem 22. The strain relief sleeve 70 is positioned over the distal tubular section 76 of the catheter lock 68. The strain relief sleeve 70 includes an internal groove 80 into which the securement ridge 78 of the catheter lock 68 fits. This serves to retain the strain relief sleeve 70 in place properly on the distal tubular section 76 of the catheter lock 68.

In use, a needle may pierce either portion of the septum 12 and fluid may then be injected into a selected one of the fluid cavities 14 or 16 for advancement through the respective channel 46 or 48 to the catheter 24. The particular construction of the fluid cavities 14 and 16 minimizes turbulence and vortex action of such fluid flow, and stagnation areas are avoided.

From the foregoing it will be appreciated that the vascular access port 10 of the present invention allows secure, direct attachment of a dual lumen catheter to the port, has no metal components, and has "seam free" inner reservoirs defined as the space between the fluid cavities 14 and 16 and the septum 12. The use of staggered outlet ducts 14a and 16a eliminates the need for a separate septum-supporting component bonded to the base 18. Since the inside of the reservoir should be as smooth as possible to help prevent damage to blood cells or initiation of blood clotting during infusion or withdrawal of blood through the port 10, the elimination of a seam created by the bonding of separable components is a significant improvement of the vascular access port 10 of the present invention relative to the prior art.

Although a particular embodiment of the invention has been described in detail for purposes of illustration, various modifications may be made without departing from the spirit and scope of the invention. Accordingly, the invention is not to be limited, except as by the appended claims.

We claim:

1. A plural reservoir vascular access port, comprising:
   a base defining a plurality of fluid cavities separated by a dividing wall configured to provide an outlet duct for each fluid cavity, wherein the outlet ducts are staggered along the length of the dividing wall;
   a cap configured to receive the base, wherein the cap includes a plurality of septum access apertures aligned with the plurality of fluid cavities;
   a septum captured between the cap and the base and providing a fluid seal between the plurality of fluid cavities and the plurality of septum access apertures; and
   an outlet from each fluid cavity outlet duct through the base.

2. The access port of claim 1, wherein the base includes elastomer-filled suture holes.

3. The access port of claim 2, wherein the suture holes are filed with silicone.

4. The access port of claim 1, wherein the base is formed of a needle-impenetrable material, and has a flat interior floor and walls normal to and upstanding therefrom, said walls defining the plurality of fluid cavities.

5. The access port of claim 4, wherein upper surfaces of the walls support the septum thereon and are co-planar.

6. The access port of claim 4, wherein at least one of the plurality of fluid cavities has a cross-section in a plane parallel to the floor of the base that is non-circular.

7. The access port of claim 1, wherein the cap includes at least one palpation ridge.

8. The access port of claim 1, wherein the outlet comprises an outlet stem connected at a proximal end thereof with the base and configured at a distal end thereof to receive a proximal end of a plural lumen catheter, the stem enclosing a plurality of channels which extend in side-by-side relationship between said distal end of said stem and the respective fluid cavity outlet duct, the channels being of different lengths and separated laterally a distance substantially equal to the lateral separation of lumens in the catheter.

9. The access port of claim 8, including means for locking the proximal end of the catheter to the outlet stem.

10. The access port of claim 9, wherein the locking means includes a rigid catheter lock slidable over the proximal end of the catheter for positioning adjacent to the base, and a resiliently flexible strain relief sleeve positionable over adjoining portions of the catheter lock and the catheter.

11. The access port of claim 10, wherein the catheter lock includes a distal tube section having a securement ridge which is fitted within an internal groove of the strain relief sleeve.

12. An implantable access port capable of being implanted beneath the skin of a patient, the access port enabling repeated, non-destructive fluid communication between the tip of a hypodermic needle piercing the skin of the patient and a proximal end of a selected one of the lumens of a plural lumen catheter implanted in the body of the patient coupled to the access port, thereby to selectively inject a fluid from the needle into the body of the patient by producing a flow of the fluid from the tip of the needle, through the access port, and along the selected one of the lumens to the distal end of the catheter, or to selectively withdraw fluid from the patient through the needle, said access port comprising:

a needle impenetrable base defining a plurality of fluid cavities separated by a dividing wall configured to provide an outlet duct for each fluid cavity, wherein the outlet ducts are staggered along the length of the dividing wall;

a cap configured to receive the base, wherein the cap includes a plurality of septum access apertures aligned with the plurality of fluid cavities;

a septum captured between the cap and the base and providing a fluid seal between the plurality of fluid cavities and the plurality of septum access apertures; and an outlet stem connected at a proximal end thereof with the base and configured at a distal end thereof to receive the proximal end of the catheter, the stem enclosing a plurality of channels which extend in side-by-side relationship between said distal end of said stem and a respective fluid cavity outlet duct, the channels being of different lengths and separated laterally a distance substantially equal to the lateral separation of the lumens in the catheter.

13. The access port of claim 12, wherein the base includes silicone-filled suture holes.

14. The access port of claim 12, wherein the base includes a flat interior floor and walls normal to and upstanding therefrom, said walls including the dividing wall and defining the plurality of fluid cavities.

15. The access port of claim 14, wherein upper surfaces of the walls support the septum thereon and are co-planar.

16. The access port of claim 12, wherein the cap includes at least one palpation ridge.

17. The access port of claim 12, including means for locking the proximal end of the catheter to the outlet stem, wherein the locking means includes a rigid catheter lock slidable over the proximal end of the catheter and the adjacent outlet stem for positioning adjacent to the base, and a resiliently flexible strain relief sleeve positionable over adjoining portions of the catheter lock and the catheter, wherein the catheter lock includes a distal tube section having a securement ridge which is fitted within an internal groove of the strain relief sleeve.

18. An implantable access port capable of being implanted beneath the skin of a patient, the access port enabling repeated, non-destructive fluid communication between the tip of a hypodermic needle piercing the skin of the patient and a proximal end of a selected one of the lumens of a dual lumen catheter implanted in the body of the patient coupled to the access port, thereby to selectively inject a fluid from the needle into the body of the patient by producing a flow of the fluid from the tip of the needle, through the access port, and along the selected one of the lumens to the distal end of the catheter, or to selectively withdraw fluid from the patient through the needle, said access port comprising:

a needle-impenetrable base having a flat interior floor and walls normal to and upstanding therefrom, the walls defining a first fluid cavity and a second fluid cavity separated by a dividing wall configured to provide a first outlet duct for the first fluid cavity and a second outlet duct for the second fluid cavity, wherein the first and second outlet ducts are staggered along the length of the dividing wall;

a needle-impenetrable cap configured to receive the base, the cap including a first septum access aperture aligned with the first fluid cavity and a second septum access aperture aligned with the second fluid cavity;

a single septum captured between the cap and the base and providing a fluid seal between the fluid cavities and the septum access apertures;

an outlet stem connected at a proximal end thereof with the base and configured at a distal end thereof to receive the proximal end of the catheter, the stem enclosing a pair of channels of different lengths which extend in side-by-side relationship between respective ones of the first and second outlet ducts and a distal end of the stem; and means for locking the proximal end of the catheter to the outlet stem.

19. The access port of claim 18, wherein the base includes silicone-filled suture holes.

20. The access port of claim 18, wherein the locking means includes a rigid catheter lock slidable over the proximal end of the catheter and the adjacent outlet stem for positioning adjacent to the base, and a resiliently flexible strain relief sleeve positionable over adjoining portions of the catheter lock and the catheter, wherein the catheter lock includes a distal tube section having a securement ridge which is fitted within an internal groove of the strain relief sleeve.

21. The access port of claim 18, including at least one palpation ridge extending upwardly from the cap adjacent to at least one of the first or second septum access apertures.

\* \* \* \* \*